United States Patent
Kang

(10) Patent No.: US 12,280,049 B2
(45) Date of Patent: Apr. 22, 2025

(54) METHODS OF DELAYING PAIN PROGRESSION AND TREATING PROSTATE CANCER

(71) Applicant: ASTRAZENECA AB, Sodertalje (SE)

(72) Inventor: Jinyu Kang, Wilmington, DE (US)

(73) Assignee: ASTRAZENECA AB, Sodertalje (SE)

( * ) Notice: Subject to any disclaimer, the term of this patent is extended or adjusted under 35 U.S.C. 154(b) by 63 days.

(21) Appl. No.: 17/392,676

(22) Filed: Aug. 3, 2021

(65) Prior Publication Data

US 2022/0040173 A1 Feb. 10, 2022

Related U.S. Application Data

(60) Provisional application No. 63/060,962, filed on Aug. 4, 2020.

(51) Int. Cl.
| | | |
|---|---|---|
| *A61K 31/502* | (2006.01) | |
| *A61K 31/498* | (2006.01) | |
| *A61P 35/00* | (2006.01) | |
| *A61P 35/04* | (2006.01) | |

(52) U.S. Cl.
CPC .......... *A61K 31/502* (2013.01); *A61K 31/498* (2013.01); *A61P 35/00* (2018.01); *A61P 35/04* (2018.01)

(58) Field of Classification Search
CPC ..... A61K 31/502; A61K 31/498; A61P 35/00; A61P 35/04; A61P 25/04
See application file for complete search history.

(56) References Cited

U.S. PATENT DOCUMENTS

| | | | |
|---|---|---|---|
| 11,136,340 B2 * | 10/2021 | Finlay | C07D 473/18 |
| 2022/0009901 A1 * | 1/2022 | Johannes | A61P 35/00 |
| 2023/0038138 A1 * | 2/2023 | Hattersley | A61K 31/5025 |

OTHER PUBLICATIONS

Mateo et al. ("DNA-Repair Defects and Olaparib in Metastatic Prostate Cancer." N Engl J Med (2015); 373:1697-1708. DOI: 10.1056/NEJMoa1506859.) (Year: 2015).*
Tannock et al. ("Docetaxel plus Prednisone or Mitoxantrone plus Prednisone for Advanced Prostate Cancer." The New England Journal of Medicine (2004); 351:1502-1512.) (Year: 2004).*
Bono, et al, "Olaparib for Metastic Castration Resistant Prostate Cancer", NEJM, 2020.
PROfound top level, Apr. 24, 2020.

* cited by examiner

*Primary Examiner* — Amanda L. Aguirre
*Assistant Examiner* — Chris E Simmons
(74) *Attorney, Agent, or Firm* — McDonnell Boehnen Hulbert & Berghoff LLP

(57) ABSTRACT

This disclosure relates to methods for delaying pain progression in a subject receiving treatment for prostate cancer. This disclosure further relates to methods for treating prostate cancer, such as for example, treating prostate cancer in a subject having pain.

18 Claims, 5 Drawing Sheets

(A)

(B)

Figure 1, continued
(C)
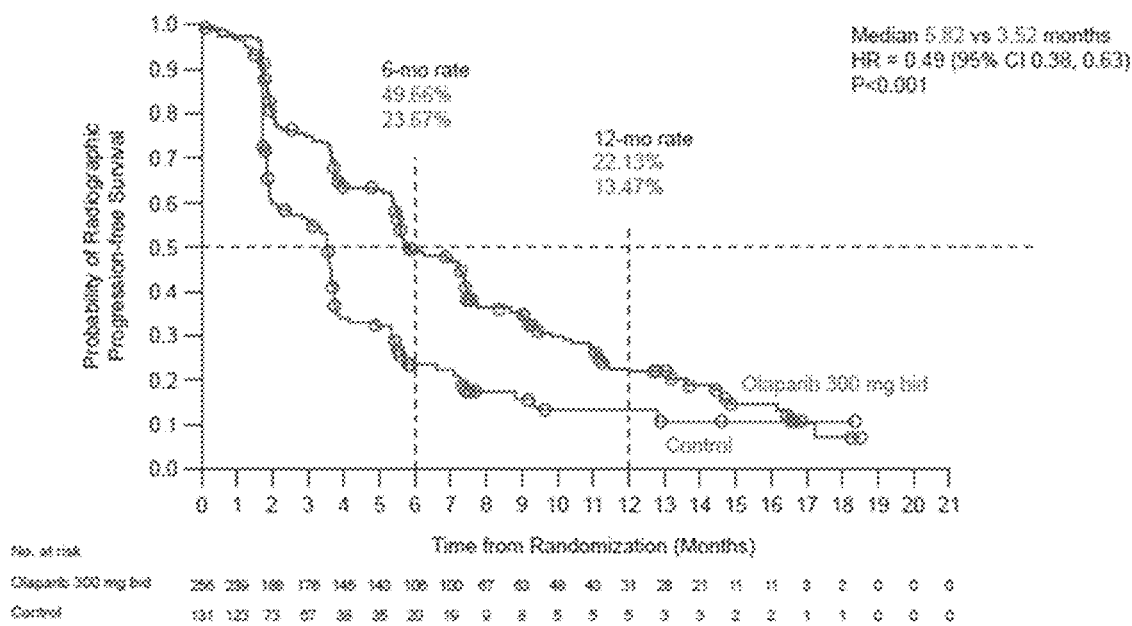
(D)
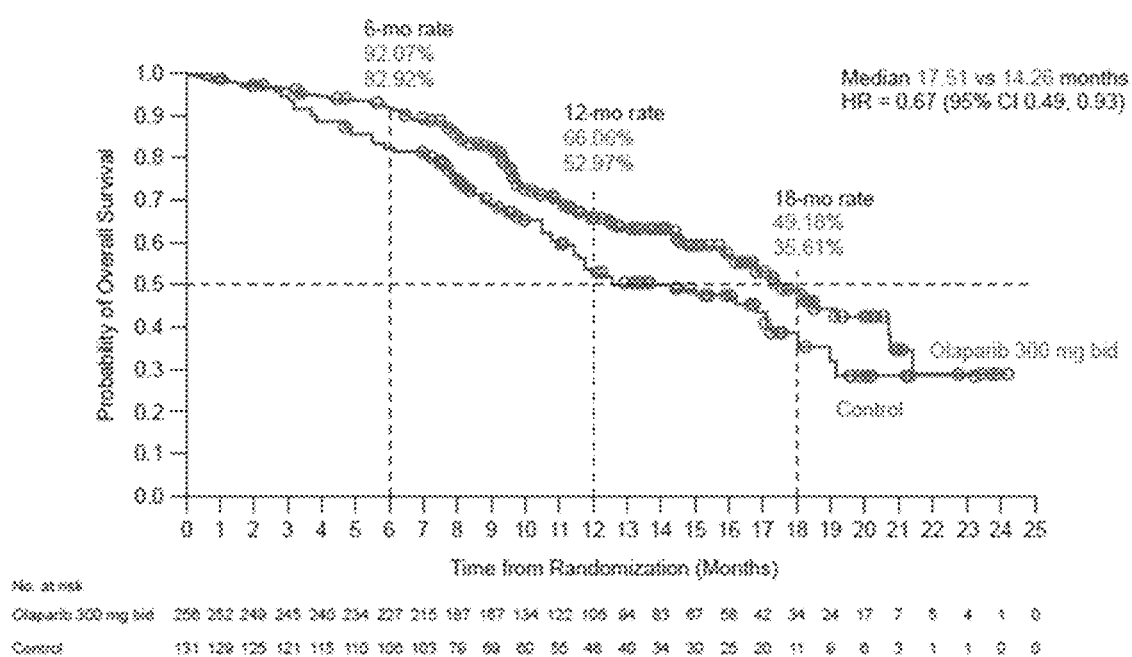

(A)

Figure 2, continued
(B)
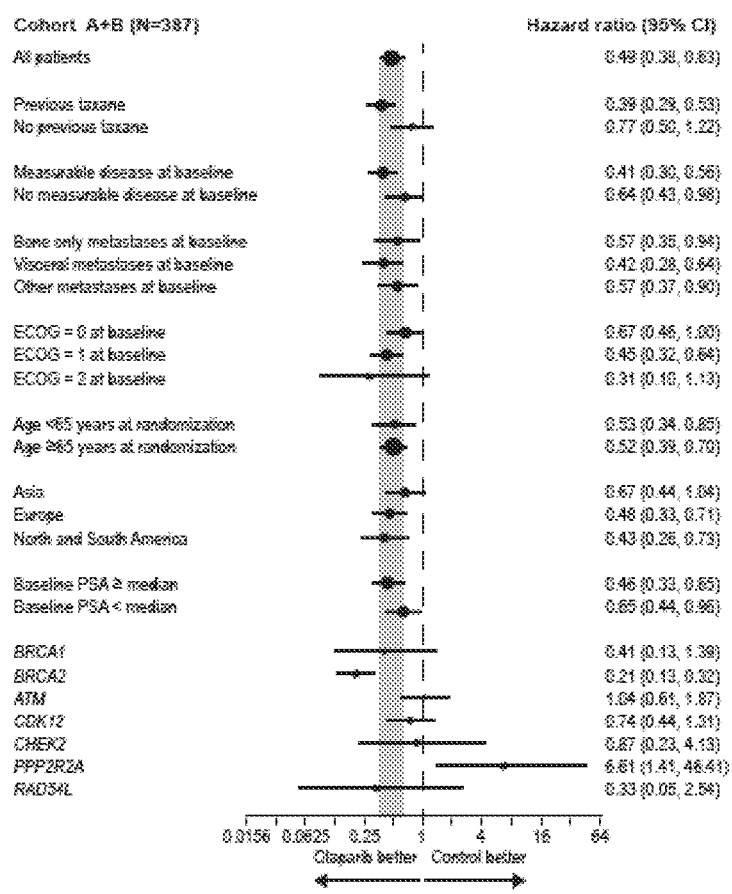

(A)

(B)

METHODS OF DELAYING PAIN PROGRESSION AND TREATING PROSTATE CANCER

BACKGROUND OF THE DISCLOSURE

Field of the Disclosure

This disclosure relates to methods for delaying pain progression in a subject receiving treatment for prostate cancer. This disclosure further relates to methods for treating prostate cancer, such as for example, treating prostate cancer in a subject having pain.

Description of Related Art

Homologous recombination (HR) has been shown to play an important role in repair of damage occurring at DNA replication forks in mammalian cells. Cells deficient in HR dependent DNA double-stranded break (DSB) repair pathway show retarded growth and exhibit higher level of genetic instability, which is believed to significantly contribute to the development of cancer in these cells. BRCA1 and BRCA 2 hereditary genes are just two out of many proteins in the HR dependent DNA DSB repair pathway. Other members of the HR dependent DNA DSB repair pathway include: ATM, BARD1, BRIP1, CHEK1, CHEK2, CDK12, FANCL, PALB2, PPP2R2A, RAD51B, RAD51C, RAD51D and RAD54L. Carriers of mutations in BRCA1 and/or BRCA2 are thus at elevated risk of various cancers, including breast, ovarian, pancreatic, and prostate cancer.

Metastatic castration-resistant prostate cancer (mCRPC) is a molecularly heterogeneous disease with poor outcomes. Tumors in up to 30% of patients with mCRPC harbor deleterious DNA damage repair gene aberrations. Among the most common of these alterations, BRCA1 and BRCA2 are well characterized homologous recombination repair (HRR) genes, and ATM functions indirectly to detect DNA damage and activate HRR. Loss-of-function alterations in these and other genes with a direct or indirect role in HRR are associated with more aggressive prostate cancers.

Molecular stratification for treatment is not currently the standard of care for metastatic prostate cancers despite evidence of substantial interpatient genomic heterogeneity. Most therapeutic strategies for advanced prostate cancers target androgen receptor signaling; taxane-based chemotherapies and radiopharmaceuticals are also approved. Although these drugs have improved outcomes in the past decade, metastatic prostate cancer remains invariably fatal and new therapeutic strategies involving molecular stratification are urgently needed.

Genomic studies of metastatic prostate cancer have identified a number of potentially actionable recurrent genomic aberrations, including loss-of-function alterations in DNA repair genes in 20-25% of cases, such as defects in HRR genes. HRR gene alterations confer sensitivity to poly (adenosine diphosphate-ribose) polymerase (PARP) inhibition in prostate and other cancers. Antitumor activity has been reported with the PARP inhibitor, olaparib, in patients with mCRPC harboring HRR gene alterations. Response to PARP inhibition may occur through multiple mechanisms, including PARP trapping, the physical obstruction of replication forks leading to DNA double strand breaks and defects in HRR.

Prostate cancer patients experience pain in all stages of the disease. In earlier stages of prostate cancer, pain can occur during urination or ejaculation, and in later cases tumors start to pressure the nearby organs and tissues and pain spreads to the pelvis, lower back, ribs, or upper thighs, and in the bones of those areas. Patients with poorly controlled pain experience significant physical effects, such as decreased strength, limited mobility, and difficulty sleeping, as well as fear, anxiety, and depression and a decrease in their overall enjoyment of life.

In the early stages of the diseases, pain is usually controlled with mild analgesics such as nonsteroidal anti-inflammatory drugs (NSAIDs), but as the disease progresses, codeine, hydrocodone, oxycodone, morphine, hydromorphone, and fentanyl, may be used to control the pain.

Therefore, there remains a need for a treatment that provides a significant delay in pain progression, and potentially an improvement in cure rates, of prostate cancer.

SUMMARY OF THE DISCLOSURE

One aspect of the disclosure provides methods for delaying pain progression in a subject receiving treatment for prostate cancer. Such methods include
administering to the subject a therapeutically effective amount of 4-[(3-{[4-(cyclopropane-carbonyl)piperazine-1-yl]carbonyl}-4-fluorophenyl)methyl]-2H-phthalazin-1-one (olaparib), or a hydrate, solvate, or prodrug thereof,
wherein the therapeutically effective amount of olaparib is sufficient to delay pain progression as evaluated by pain questionnaire and/or an opioid use log in the subject as compared to pain progression in the subject receiving a new hormonal agent.

Another aspect of the disclosure provides methods for treating prostate cancer in a subject having pain. Such methods include:
administering to the subject a therapeutically effective amount of 4-[(3-{[4-(cyclopropane-carbonyhpiperazine-1-yl]carbonyl}-4-fluorophenyl)methyl]-2H-phthalazin-1-one (olaparib), or a hydrate, solvate, or prodrug thereof,
wherein the therapeutically effective amount of olaparib is sufficient to delay pain progression as evaluated by pain questionnaire and/or an opioid use log in the subject as compared to pain progression in the subject receiving a new hormonal agent.

Yet another aspect of the disclosure provides methods for treating prostate cancer in a subject. Such methods include:
administering to the subject a therapeutically effective amount of 4-[(3-{[4-(cyclopropane-carbonyl)piperazine-1-yl]carbonyl}-4-fluorophenyl)methyl]-2H-phthalazin-1-one (olaparib), or a hydrate, solvate, or prodrug thereof,
wherein the median progression free survival (or other therapeutic metric such as overall survival, prostate-specific antigen response, and/or circulating tumor cell conversion rate) is improved by about 2 to 5 months over the standard of care (e.g., over receiving a new hormonal agent).

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The accompanying drawings are included to provide a further understanding of the compositions and methods of the disclosure, and are incorporated in and constitute a part of this specification. The drawings illustrate one or more embodiment(s) of the disclosure and, together with the description, serve to explain the principles and operation of the disclosure.

DETAILED DESCRIPTION OF THE DISCLOSURE

Figure 1:
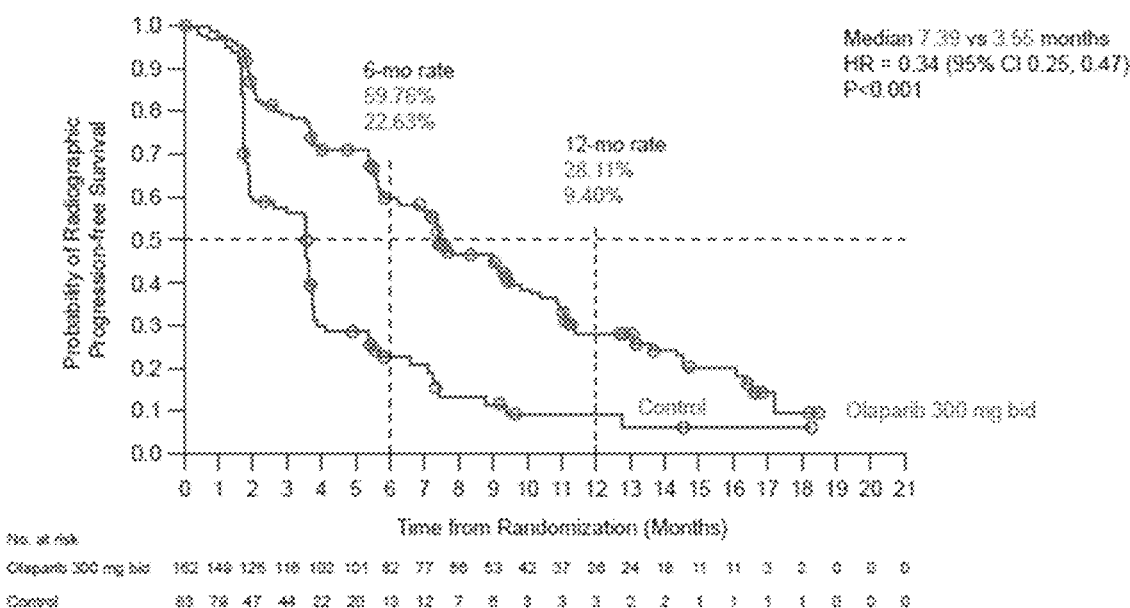
FIG. 1 shows Kaplan-Meier estimates of (A) radiographic progression-free survival (rPFS) by blinded independent central review and (B) interim overall survival (OS) in patients with alterations in BRCA1, BRCA2, and/or ATM (Cohort A), and (C) radiographic progression-free survival and (D) interim OS in patients in the overall population. For censored patients in Cohort A: the median duration of follow-up for radiographic progression-free survival was 7.39 months in the olaparib group and 3.55 months in the control group; the median duration of follow-up for overall survival was 18.50 months and 15.11 months, respectively. For censored patients in the overall population (Cohorts A+B): the median duration of follow-up for rPFS was 5.82 months in the olaparib group and 3.52 months in the control group; the median duration of follow-up for overall survival was 17.51 months and 14.26 months, respectively. Overall, at the time of the rPFS analysis by blinded independent central review (BICR), 9 (5.6%) olaparib patients and 4 (4.8%) control arm patients had withdrawn consent and were censored.
Figure 1:
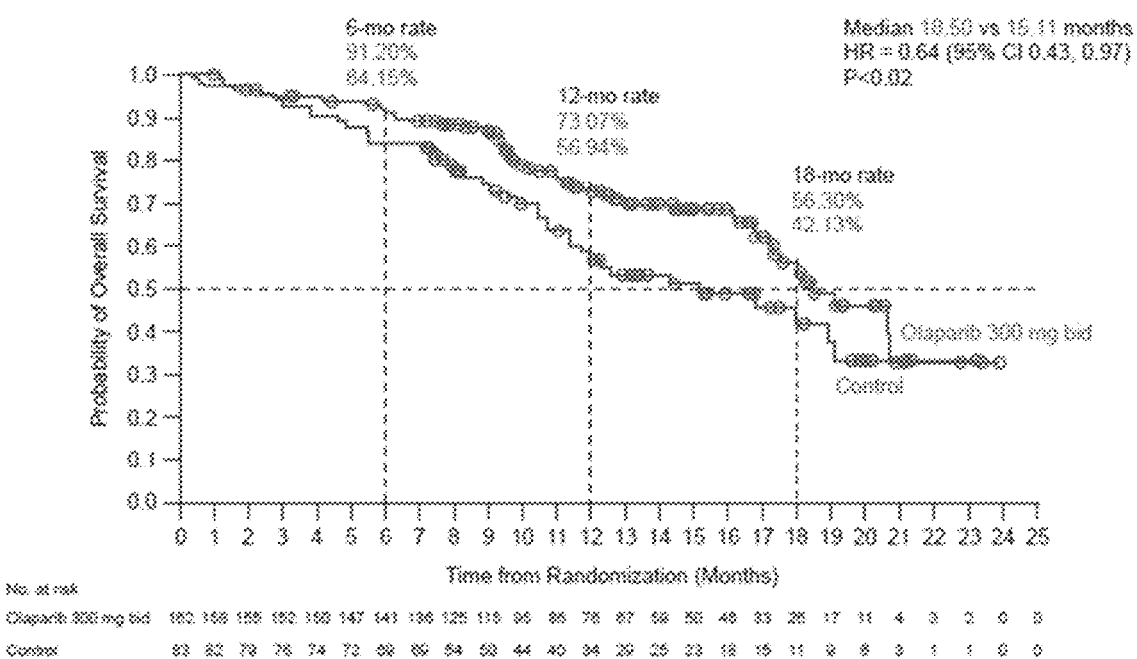

Before the disclosed processes and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

In view of the present disclosure, the methods and compositions described herein can be configured by the person of ordinary skill in the art to meet the desired need. The present disclosure provides improvements in treating prostate cancer. The present disclosure also provides improvements in delaying pain progression in a subject receiving treatment for prostate cancer.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof, or inhibiting the progression of disease; or (ii) eliciting the referenced biological effect (e.g., inducing apoptosis, or inhibiting glutathione synthesis).

Thus, one aspect of the disclosure includes methods for delaying pain progression in a subject receiving treatment for prostate cancer. Another aspect of the disclosure provides methods for treating prostate cancer in a subject, for example, in a subject having pain.

The methods of the disclosure include administering to the subject a therapeutically effective amount of 4-[(3-{[4-(cyclopropane-carbonyhpiperazine-1-yl]carbonyl}-4-fluorophenyl)methyl]-2H-phthalazin-1-one (olaparib), or a hydrate, solvate, or prodrug thereof.

As provided above, in the methods of the disclosure, the cancer is prostate cancer. In certain embodiments, the cancer is prostate cancer that has metastasized. For example, the metastasis is to bone. In certain embodiments, the cancer is metastatic castration-resistant prostate cancer (mCRPC).

Another embodiment of the disclosure provides methods where the prostate cancer is homologous recombination deficient (HRD) cancer. For example, whether the cancer is HRD positive can be determined by Myriad Genetics myChoice® HRD or myChoice® HRD Plus assay. In certain other embodiments, the methods of the disclosure further comprise identifying the subject having cancer cells comprising one or more HRR gene mutations.

In certain other embodiments of the methods of the disclosure, the prostate cancer comprises one or more HRR gene mutations. As used herein, the HHR gene mutation includes deleterious or suspected deleterious, germline or somatic mutations.

In certain embodiments, the cancer cells comprise HRR gene mutation selected from BRCA1, BRCA2, ATM, BRIP1, BARD1, CDK12, CHEK1, CHEK2, FANCL, PALB2, PPP2R2A, RAD51B, RAD51C, RAD51D, and RAD54L gene mutation. In certain embodiments, the cancer cells comprise a BRCA1, a BRCA2, and/or an ATM gene mutation. In certain other embodiments, the methods of the disclosure further comprise identifying the subject having cancer cells comprising a BRCA1, a BRCA2, and/or an ATM gene mutation.

In certain embodiments, the cancer cells comprise a BRCA1 and/or a BRCA2 gene mutation. In certain embodiments, the cancer cells comprise an ATM gene mutation.

In certain embodiments, the cancer cells comprises a BRIP1, a BARD1, a CDK12, a CHEK1, a CHEK2, a FANCL, a PALB2, a PPP2R2A, a RAD51B, a RAD51C, a RAD51D, and/or a RAD54L gene mutation.

In certain other embodiments of the methods of the disclosure, the prostate cancer is metastatic castration-resistant prostate cancer (mCRPC) comprising one or more homologous recombination repair (HRR) gene mutations.

As used herein, the terms "individual," "patient," or "subject" are used interchangeably, refers to any animal, including mammals, and most preferably humans.

The methods of disclosure are useful as a second line treatment. Thus, in certain embodiments of the methods of the disclosure, the subject has previously received a first line of therapy. The methods of the disclosure, in certain embodiments, may provide a delay in progression and relapse of cancer of subjects that have previously received or completed a first line of chemotherapy. For example, in certain embodiments, the subject has previously received or completed a first line platinum-taxane based chemotherapy. In certain other embodiments, the subject previously received or completed new hormonal agent (NHA) chemotherapy. For example, the new hormonal agent may be enzalutamide or abiraterone.

In certain other embodiments of the methods of the disclosure, the prostate cancer is metastatic castration-resistant prostate cancer (mCRPC) comprising one or more homologous recombination repair (HRR) gene mutations, and the subject has previously received enzalutamide or abiraterone.

The methods of the disclosure are also useful as a first line treatment. Thus, in certain embodiments of the methods of the disclosure, the subject received no prior therapy.

As will be discussed in more detail below, the methods of the disclosure may be particularly useful in subject having pain (e.g., pain that is associated with prostate cancer, including but not limited to pain during urination, during ejaculation, pelvis, lower back, ribs, upper thighs, etc.). In certain embodiments, the subject is identified as having pain based on Brief Pain Inventory-Short Form item 3 ('worst pain in 24 hours"). In certain embodiments, the subject is identified as having pain based on initiation of opiate analgesic use (Analgesic Quantification Algorithm score). In certain embodiments, the subject is identified as having pain based on Brief Pain Inventory-Short Form item 3 and initiation of opiate analgesic use. In certain other embodiments, the methods of the disclosure further comprise identifying the subject having pain.

As provided above, the methods of the disclosure as described herein require administration of olaparib. As used herein, "olaparib" refers to 4-[(3-{[4-(cyclopropane-carbonyhpiperazine-1-yl]carbonyl}-4-fluorophenyhmethyl]-2H-phthalazin-1-one, or a hydrate, solvate, or prodrug thereof. 4-[(3-{[4-(cyclopropane-carbonyhpiperazine-1-yl]carbonyl}-4-fluorophenyhmethyl]-2H-phthalazin-1-one, having the following structure, is disclosed in International Publication No. WO 2004/080976 A1, incorporated by reference herein.

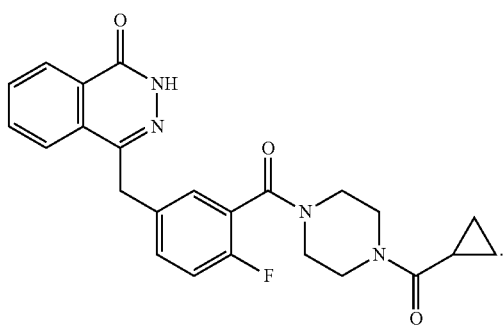 [SMILES: O=C(c1cc(Cc2n[nH]c(=O)c3ccccc23)ccc1F)N1CCN(C(=O)C2CC2)CC1]

Olaparib is administered preferably in the form of a pharmaceutical composition. Therapeutically effective amount of olaparib has been previously established. For example, in certain embodiments, the therapeutically effective amount of olaparib is in the range of about 400 to 800 mg per day. For example, in certain embodiments, olaparib is administered in an amount of about 600 mg daily (e.g., about 300 mg taken twice daily).

The inventors unexpectedly found that administering olaparib is sufficient to delay pain progression in the subject as compared to pain progression in the subject not receiving olaparib (e.g., the subject receiving the standard of care treatment such as a new hormonal agent treatment). Therefore, in the methods of the disclosure the therapeutically effective amount of olaparib is sufficient to delay pain progression in the subject as compared to pain progression in the subject receiving a new hormonal agent, as evaluated by pain questionnaire and/or an opioid use log.

In certain embodiments, the therapeutically effective amount of olaparib reduces the risk of pain progression by at least 30% compared to subject receiving the standard of care treatment. For example, in certain embodiments, the risk of pain progression is reduced by at least 40%, e.g., at least 45%, or at least 50%, or at least 55%.

In certain embodiments, the therapeutically effective amount of olaparib delays pain progression by at least 4 months. For example, in certain embodiments, the pain progression is delayed by at least 5 months, or 6 months, or 7 months, or 8 months, or 9 months, or even 10 months.

Pain that is associated with prostate cancer may require treatment with a pain-reducing therapy, such as an opiate. As used herein, "opiate" includes any opiate or an opiate-like drug (e.g. an opioid). Examples include, but are not limited to, codeine, hydrocodone, oxycodone, morphine, hydromorphone, and fentanyl.

Thus, in certain embodiments, the methods of the disclosure further comprise administering an opiate. The inventors unexpectedly found that administering olaparib is sufficient to delay the administration of the opiate as compared to administration of an opiate in the subject receiving the standard of care treatment, e.g. a new hormonal agent. In certain embodiments, the therapeutically effective amount of olaparib delays opiate administration by at least 4 months. For example, in certain embodiments, the opiate administration is delayed by at least 5 months, or 6 months, or 7 months, or 8 months, or 9 months, or even 10 months.

In certain embodiments, administering olaparib is sufficient to decrease the therapeutically effective amount of the opiate as compared to the therapeutically effective amount of an opiate in the subject receiving the standard of care treatment, e.g. a new hormonal agent. For example, the subject may require less frequent administration of the opiate.

The inventors also unexpectedly found that administering olaparib is sufficient to improve progression free survival (or other key therapeutic metric such as overall survival, prostate-specific antigen response, and/or circulating tumor cell conversion rate) in the subject as compared to the subject receiving the standard of care treatment (e.g., over receiving a new hormonal agent). For example, in the overall subject population, the inventors found that the median progression free survival is at least about 2 months greater than for subjects receiving the standard of care treatment. In certain embodiments, the median progression free survival is improved by about 2 to about 5 months (e.g., about 2 to about 4 months, or about 2 to about 3 months, or about 3 to about 5 months, or about 3 to about 4 months, or about 4 to about 5 months).

As used herein, the phrase "therapeutically effective amount" or "effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, an effective amount can be an amount suitable for
  (i) inhibiting the progression the disease;
  (ii) prophylactic use for example, preventing or limiting development of a disease, condition or disorder in an individual who may be predisposed or otherwise at risk to the disease, condition or disorder but does not yet experience or display the pathology or symptomatology of the disease;

(iii) inhibiting the disease; for example, inhibiting a disease, condition or disorder in an individual who is experiencing or displaying the pathology or symptomatology of the disease, condition or disorder;

(iv) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (v) eliciting the referenced biological effect.

EXAMPLE

The methods of the disclosure are illustrated further by the following example, which is not to be construed as limiting the disclosure in scope or spirit to the specific procedures and compounds described in them.

Methods

Patient population. In clinical trial NCT02987543, eligible patients were male, aged ≥18 years with histological diagnosis of prostate cancer, confirmed mCRPC, whose disease had progressed after one or more treatments with new hormonal agent (NHA) (e.g., enzalutamide or abiraterone, administered for metastatic or non-metastatic castration-resistant prostate cancer, as well as metastatic hormone-sensitive prostate cancer). Prior taxane chemotherapy was allowed. Men without prior surgical castration were required to continue luteinizing-hormone-releasing hormone analog therapy. Patients had adequate organ and bone marrow function. Full eligibility criteria are provided in the trial protocol. All patients provided written informed consent. An investigational clinical trial assay, based on the FoundationOne® CDx next-generation sequencing test was used to prospectively identify patients with qualifying deleterious or suspected deleterious alterations in one or more of the 15 prespecified genes selected for their direct or indirect role in HRR: BRCA1, BRCA2, ATM, BRIP1, BARD1, CDK12, CHEK1, CHEK2, FANCL, PALB2, PPP2R2A, RAD51B, RAD51C, RAD51D, and RAD54L. Tumor testing was conducted centrally using archival or recent biopsy tissue from primary or metastatic disease. Presence of deleterious or suspected deleterious alteration by the central tumor test was required for eligibility, irrespective of the zygosity of the alteration.

Overall, 4425 patients were enrolled for screening at 206 sites in 20 countries; 4047 patients had tumor tissue available for testing, among whom 2792 (69.0%) were successfully sequenced with a biomarker status outcome reported. A qualifying alteration in ≥1 of the prespecified genes with a direct or indirect role in HRR was detected in 778/2792 (27.9%) patients. Of these, 387 (49.7%) met all eligibility criteria and were thus randomized.

Study design. This was a prospective, randomized, open-label, Phase III study. Eligible patients were included in one of two cohorts depending on their qualifying gene alteration. Cohort A included patients with BRCA1, BRCA2 and/or ATM alterations, regardless of co-occurring qualifying alterations in any of the other genes. Cohort B included patients with alterations in any of the other 12 genes. The overall population comprised patients from Cohort A and Cohort B (i.e., patients with a qualifying alteration in any of the 15 prespecified genes).

A central interactive voice or web response system was used to randomly assign patients in a 2:1 ratio to receive 1) the standard dose of olaparib tablets (300 mg twice daily [bid]) (olaparib arm) or 2) pre-declared physician's choice of enzalutamide (160 mg once daily [qd]) or abiraterone (1000 mg qd) plus prednisone (5 mg bid) (control arm). Randomization was stratified by previous taxane use (yes/no) and measurable disease (yes/no). Treatment was continued until objective radiographic disease progression assessed by a third-party vendor blinded independent central review (BICR), or unacceptable toxicity. Patients randomized to the control arm were eligible to cross over to olaparib treatment upon BICR-confirmed radiographic progression.

The primary endpoint was rPFS assessed by BICR in patients with BRCA1, BRCA2, and/or ATM alterations (Cohort A). rPFS was defined as the time from randomization until soft-tissue disease progression (by Response Evaluation Criteria in Solid Tumors (RECIST) v1.1), bone lesion progression (by Prostate Cancer Working Group 3 (PCWG3) criteria) or death. A prespecified sensitivity analysis of rPFS based on investigator assessment was performed. rPFS by BICR in the overall population was also a secondary endpoint.

Additional secondary endpoints evaluated included confirmed radiographic objective response rate (ORR), time to pain progression (TTPP), overall survival (OS), prostate-specific antigen (PSA) response ($PSA_{50}$ response) and circulating tumor cell (CTC) conversion rate. ORR was assessed among evaluable patients who had measurable disease at baseline as assessed by BICR using RECIST v1.1 (responses were also assessed by BICR using RECIST v1.1, were confirmed and required absence of progression on bone scan assessed by PCWG3). OS is defined as time from randomization to time point at which death due to any cause occurs. A pre-specified sensitivity analysis for the crossover effect on OS was performed. Safety was assessed in the overall population through reporting of Common Terminology Criteria for Adverse Events (CTCAE) v4.0 and collection of clinical chemistry and hematology parameters.

Time to pain progression (TTPP) was based on Brief Pain Inventory-Short Form item 3 ('worst pain in 24 hours) and initiation of opiate analgesic use (Analgesic Quantification Algorithm score). Specifically, TTPP is defined as time from randomization to time point at which worsening in pain (based on Brief Pain Inventory-Short Form item 3) is observed (i.e. date of pain progression—date of randomization+1 day) for asymptomatic patients and symptomatic patients (at baseline). $PSA_{50}$ response is defined as the proportion of patients achieving a ≥50% decrease in PSA from baseline to the lowest post-baseline PSA result, confirmed by a second consecutive PSA assessment at least 3 weeks later. Circulating tumor cell (CTC) conversion rate was defined as the proportion of patients achieving a decline in the number of CTCs from ≥5 cells/7.5 mL at baseline to <5 cells/7.5 mL post-baseline (Veridex™). Patients evaluable for PSA response and CTC conversion rate were those with a valid baseline and post-baseline PSA measurement and CTC count measurement, respectively; for CTC conversion analyses, only patients with baseline values ≥5 cells/7.5 mL at baseline were included.

Soft-tissue computed tomography (CT) or magnetic resonance imaging (MRI) of the chest, abdomen, and pelvis, as well as bone scans (using bone scintigraphy commonly performed with technetium-99), were conducted at baseline and then every 8 weeks until disease progression. Bone lesions were assessed by bone scans and were separate to the Response Evaluation Criteria in Solid Tumors version 1.1 malignant soft-tissue assessment. In line with the Prostate Cancer Working Group 3 criteria, positive hot spots on the bone scans were considered significant and unequivocal sites of malignant disease and were recorded as metastatic bone lesions.

Blood samples for PSA assessments were collected at baseline, every 4 weeks until week 24, then every 8 weeks until study treatment discontinuation, and for CTC analyses were collected at baseline and then every 8 weeks until study treatment discontinuation. Overall survival was assessed every 12 weeks after progression. Adverse events (AEs) were graded according to the National Cancer Institute Common Terminology Criteria for Adverse Events version 4.0.

Subsequent therapies and crossover to olaparib. Subsequent therapies were administered at the investigators' discretion. For patients randomized to the comparator arm who had blinded independent central review (BICR)-confirmed progression, access to olaparib (300 mg bid) was allowed if they had not received any subsequent anticancer therapy following discontinuation of randomized treatment and any unresolved toxicities from prior therapy were controlled and were grade ≤1 at the time of initiating olaparib treatment. If patients were not eligible for or chose not to switch to olaparib, subsequent therapies were administered at the investigators' discretion. For patients who were randomized to receive physician's choice of treatment who subsequently switched to olaparib treatment following progression, safety data were summarized according to the treatment they received at the time of the onset of the AE or laboratory result. Tumor assessment by bone scan and CT/MRI was ceased, but follow-up for second progression and survival continued.

Statistical analysis. Efficacy data were analyzed on an intent-to-treat basis and safety data were reported for all patients who received ≥1 dose of trial treatment. With a sample size of about 240 patients in Cohort A, 143 rPFS events (approximately 60% maturity) would provide the trial with 95% power, at a two-sided significance level of 5%, to show a significant difference in rPFS between the olaparib and control groups, assuming a hazard ratio of 0.53. For time-to-event endpoints, rPFS, time to pain progression, and OS, P-values were calculated using log-rank tests, stratified by stratification factors. Hazard ratios and 95% confidence intervals (Cis) were calculated using Cox proportional hazards models, with stratification factors as covariates. The Kaplan-Meier method was used to calculate medians for each trial arm. Logistic regression models adjusted for stratification factors were used to analyze objective responses. A multiple-testing procedure was used to control for the study-wide type 1 error rate. If the primary endpoint of rPFS in Cohort A demonstrated statistical significance, testing of key secondary endpoints was performed in a hierarchical manner: objective response rate (Cohort A), rPFS (overall population), time to pain progression (Cohort A), and OS (Cohort A), with the two-sided 5% level of alpha recycled sequentially. For OS, the two-sided 5% level of alpha was split at the interim (0.01) and final (0.047) analyses using an O'Brien-Fleming spending function.

Results

In Cohort A, 162 patients were randomized to olaparib and 83 to the control arm. In Cohort B, 94 patients were randomized to olaparib, and 48 to the control arm. While baseline parameters appeared balanced overall, the control arm had a higher proportion of patients with visceral metastases and a higher median baseline PSA, and the olaparib arm included a greater proportion of patients with an ATM alteration (Table 1).

TABLE 1

Characteristics of Patients at Baseline

| Characteristic | Patients with alterations in BRCA1, BRCA2, and/or ATM (Cohort A) | | Patients in the overall population (Cohorts A + B) | |
|---|---|---|---|---|
| | Olaparib (N = 162) | Control arm (N = 83) | Olaparib (N = 256) | Control arm (N = 131) |
| Age at randomization, years, median (range) | 68 (47-86) | 67 (49-86) | 69 (47-91) | 69 (49-87) |
| Age ≥65 years at randomization, n (%) | 108 (66.7) | 60 (72.3) | 174 (68.0) | 97 (74.0) |
| Metastatic disease at initial diagnosis, n (%) | 38 (23.5) | 19 (22.9) | 66 (25.8) | 25 (19.1) |
| Missing | 7 (4.3) | 4 (4.8) | 11 (4.3) | 7 (5.3) |
| Gleason score ≥ 8,* n (%) | 105 (66.9) | 54 (67.5) | 183 (72.9) | 95 (74.8) |
| Patients with alteration(s) in a single gene,† n (%) | | | | |
| BRCA1 | 8 (4.9) | 5 (6.0) | 8 (3.1) | 5 (3.8) |
| BRCA2 | 80 (49.4) | 47 (56.6) | 81 (31.6)* | 47 (359) |
| ATM | 60 (37.0) | 24 (28.9) | 62 (24.2) | 24 (18.3) |
| CDK12 | — | — | 61 (23.8) | 28 (21.4) |
| Baseline PSA, pg/L, median (Q1, Q3) | 62.2 (21.9, 280.4) | 112.9 (34.3, 317.1) | 68.2 (24.1, 294.4) | 106.5 (37.2, 326.6) |
| Measurable disease at baseline,‡ n (%) | 95 (58.6) | 46 (55.4) | 149 (58.2) | 72 (55.0) |
| Metastases at baseline,‡ n (%) | | | | |
| Bone only | 57 (35.2) | 23 (27.7) | 86 (33.6) | 38 (29.0) |
| Visceral (lung/ liver) | 46 (28.4) | 32 (38.6) | 68 (26.6) | 44 (33.6) |
| Other | 49 (30.2) | 23 (27.8) | 88 (34.4) | 41 (31.3) |

TABLE 1-continued

Characteristics of Patients at Baseline

| | Patients with alterations in BRCA1, BRCA2, and/or ATM (Cohort A) | | Patients in the overall population (Cohorts A + B) | |
|---|---|---|---|---|
| Characteristic | Olaparib (N = 162) | Control arm (N = 83) | Olaparib (N = 256) | Control arm (N = 131) |
| ECOG performance status, n (%) | | | | |
| 0 | 84 (51.9) | 34 (41.0) | 131 (51.2) | 55 (42.0) |
| 1 | 67 (41.4) | 46 (55.4) | 112 (43.8) | 71 (54.2) |
| 2 | 11 (6.8) | 3 (3.6) | 13 (5.1) | 4 (3.1) |
| Missing | 0 | 0 | 0 | 1 (0.8) |
| Prior new hormonal agent, n (%)¥ | | | | |
| Enzalutamide only | 68 (42.0) | 40 (48.2) | 105 (41.0) | 54 (41.2) |
| Abiraterone only | 62 (38.3) | 29 (34.9) | 100 (39.1) | 54 (41.2) |
| Abiraterone + enzalutamide | 32 (19.8) | 14 (16.9) | 51 (19.9) | 23 (17.6) |
| Previous taxane use, n (%) | 106 (65.4) | 52 (62.7) | 170 (66.4) | 84 (64.1) |
| Docetaxel only | 74 (45.7) | 32 (38.6) | 115 (44.9) | 58 (44.3) |
| Cabazitaxel only | 2 (1.2) | 0 (0.0) | 3 (1.2) | 0 (0.0) |
| Docetaxel + cabazitaxel | 29 (17.9) | 20 (24.1) | 51 (19.9) | 26 (19.8) |
| Paclitaxel only | 1 (0.6) | — | 1 (0.4) | — |

Figure 2:
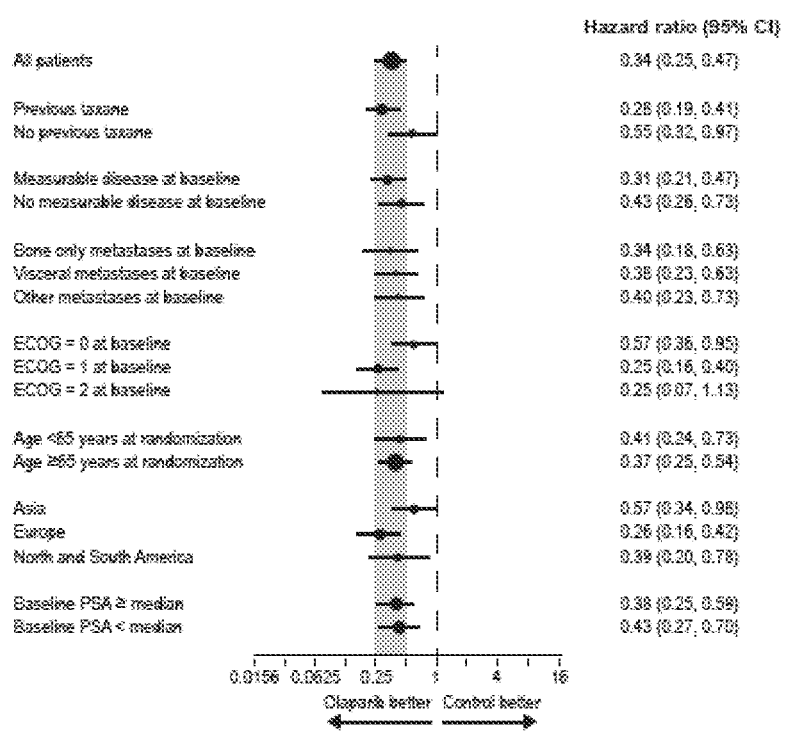
FIG. 2 shows prespecified subgroup analysis of radiographic progression-free survival by blinded independent central review among (A) patients with an alteration in BRCA1, BRCA2, and/or ATM (Cohort A) and (B) patients in the overall population. Subgroups in which fewer than five progression-free survival events occurred per group were not included in the analysis. The sizes of the circles are proportional to the number of events. The dashed line indicates the point of no effect (hazard ratio=1). A hazard ratio of less than 1 favors olaparib.

*Based on patients with non-missing data
†Twenty-eight patients (21 patients in Cohort A and seven patients in Cohort B) had mutations in more than one gene. Four patients were incorrectly assigned to Cohort B (one BRCA2 [olaparib], one BRCA2+ CDK12 [control]and two ATM [both olaparib])
‡Derived from electronic case report forms
¥Thirteen patients received NHA for disease prior to mCRPC, all others received NHA for mCRPC ECOG, Eastern Cooperative Oncology Group; PSA, prostate-specific antigen; SD, standard deviation Patients with an alteration in BRCA1, BRCA2, and/or ATM (Cohort A). Analysis of the primary endpoint was performed after 174/245 patients in Cohort A had experienced radiographic progression by BICR or had died (data maturity, 71). The median rPFS was significantly longer in the olaparib group compared with the control group (median 7.39 vs 3.55 months; hazard ratio 0.34, 95% CI 0.25 to 0.47; P<0.001; FIG. 1A). A prespecified sensitivity analysis based on investigator assessment yielded similar results to the primary analysis (hazard ratio 0.24, 95% CI, 0.17 to 0.34). Prespecified subgroup analyses are shown in FIG. 2.

Figure 3:
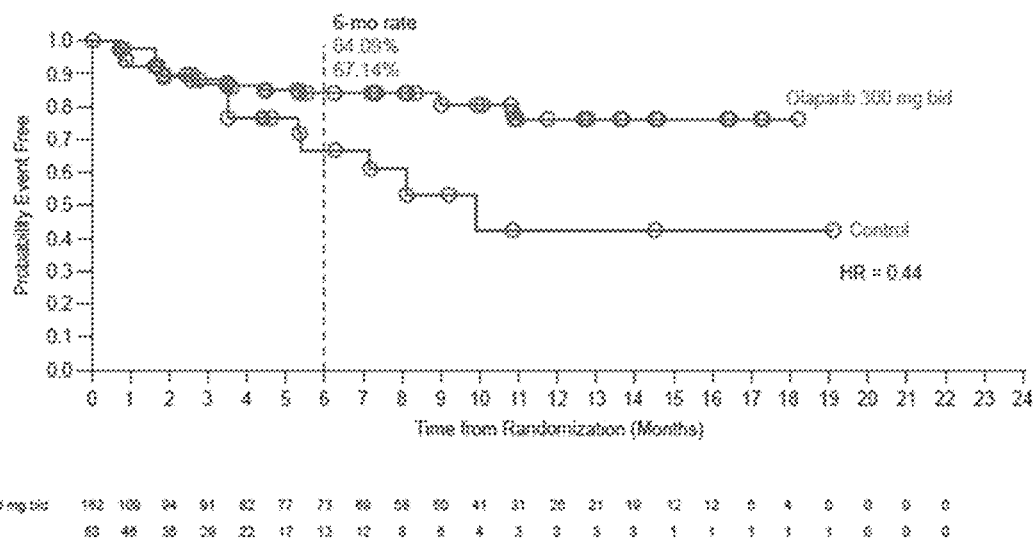
FIG. 3 shows time to pain progression among patients with alterations in (A) BRCA1, BRCA2, or ATM (Cohort A) and (B) the overall population. Time to pain progression was based on the brief pain inventory-short form worst pain [Item 3] and opioid use.
Figure 3:
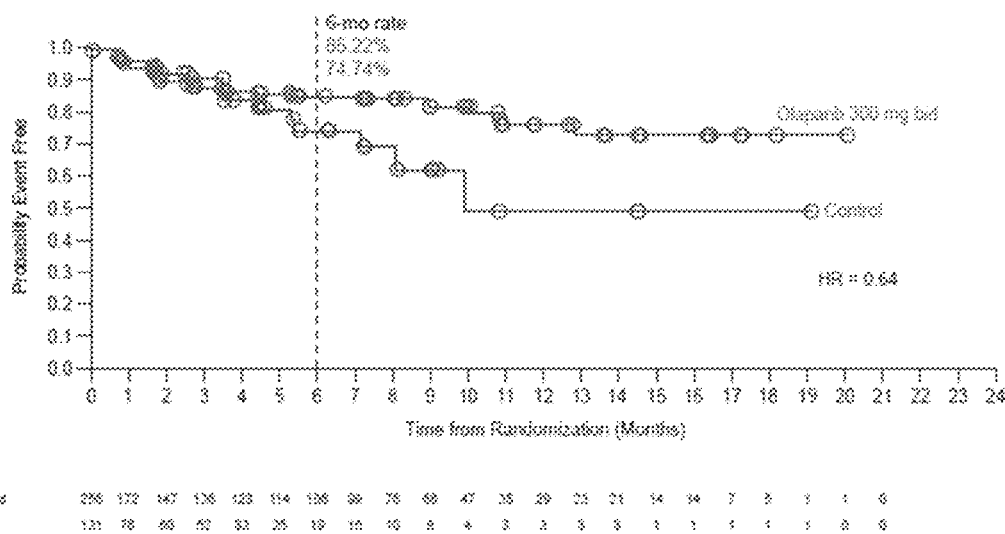

Confirmed objective response rate among evaluable patients was 33.3% (28/84 patients) in the olaparib arm versus 2.3% (1/43 patients) in the control arm (odds ratio 20.86, 95% CI 4.18 to 379.18; P<0.001). Median time to pain progression was significantly improved in the olaparib versus the control arm among patients in Cohort A (hazard ratio 0.44; 95% CI 0.22 to 0.91; P=0.02; FIG. 3A). A sensitivity analysis including death as an event in the absence of pain progression yielded similar results (Table 2). At this time, an interim analysis for OS was also conducted when 93/245 patients had died (data maturity, 38%) and yielded a median OS of 18.50 months with olaparib versus 15.11 months with the control treatment (hazard ratio 0.64, 95% CI, 0.43 to 0.97; P=0.02; FIG. 1B). Among the control arm patients with BICR-confirmed radiographic disease progression, 80.6% crossed over to olaparib treatment at the investigators' discretion.

TABLE 2

Time to pain progression (TTPP) sensitivity analysis, including any death as an event in the absence of pain progression

| Cohort A | Olaparib (n = 162) | Control arm (n = 83) |
|---|---|---|
| Median TTPP (months) | 17.22 | 5.45 |
| Hazard ratio (95% CI) | 0.501 (0.303 to 0.849) | |
| P value | 0.0068 | |
| Cohorts A + B (Overall population) | Olaparib (n = 256) | Control arm (n = 131) |
| Median TTPP (months) | 11.89 | 6.93 |
| Hazard ratio (95% CI) | 0.596 (0.395 to 0.917) | |
| P value | 0.0124 | |

Among evaluable patients, 43.1% (66/153) in the olaparib arm and 7.8% (6/77) in the control arm had a $PSA_{50}$ response. CTC conversion was observed in 29.9% (29/97) and 11.4% (5/44) of evaluable patients in the olaparib and control arms, respectively.

In the overall population, TTPP for worst pain and pain severity favored patients receiving olaparib compared with control arm at both the 6- and 12-month rate, as did time to opiate use (Table 3).

TABLE 3

Time to pain progression (TTPP) sensitivity analysis, at 6-months and 12-minths, in Cohorts A + B (overall population)

| TTPP | | 6-month rate (%) | 12-month rate (%) | Events n (%) | Median (m) | HR (95% CI) | P value (nominal) |
|---|---|---|---|---|---|---|---|
| Worst pain | Olaparib | 85.2 | 76.3 | 32 (12.5) | — | 0.64 (0.35, 1.21) | 0.149 |
|  | control | 74.7 | 50.5 | 16 (12.2) | — |  |  |
| Pain severity | Olaparib | 88.7 | 81.0 | 24 (9.4) | — | 0.71 (0.35, 1.54) | 0.411 |
|  | control | 81.5 | 65.2 | 11 (8.4) | — |  |  |
| Opiate use | Olaparib | 25 | 41 | 65 (37.1) | 18.0 | 0.67 (0.46, 0.99) | 0.0229 |
|  | control | 39 | 52 | 44 (47.8) | 9.0 |  |  |

Patients with a qualifying alteration in any prespecified gene with a direct or indirect role in HRR (overall population). In the overall population, the median rPFS by BICR was significantly longer in the olaparib group compared with the control group (hazard ratio 0.49, 95% CI, 0.38 to 0.63; P<0.001; median 5.82 vs. 3.52 months, respectively; FIG. 1C). This finding was supported by sensitivity analysis by investigator assessment (data not shown). Exploratory rPFS findings for individual genes are reported in FIG. 2.

In evaluable patients, confirmed objective response rate was 21.7% (30/138 patients) in the olaparib arm and 4.5% (3/67 patients) in the control arm (odds ratio 5.93, 95% CI, 2.01 to 25.40). After 6 months, 85.2% of patients in the olaparib arm were free of pain progression, compared to 74.7% in the control arm (FIG. 3B). Median OS at interim analysis (data maturity, 41%) was 17.51 months and 14.26 months in the olaparib and control arms, respectively (hazard ratio 0.67, 95% CI, 0.49 to 0.93; FIG. 1D); crossover to olaparib from the control arm in patients with BICR-confirmed radiographic progression was 81.8%.

A $PSA_{50}$ response was confirmed in 30.0% (73/243) of evaluable olaparib-arm patients in the overall population versus 9.8% (12/123) of evaluable control-arm patients. Among evaluable patients, 26.8% (41/153) in the olaparib group and 10.3% (7/68) in the control group had CTC conversion.

There was a statistically significant and clinically meaningful improvement in rPFS in the olaparib arm compared with the control arm for patients with an alteration in BRCA1, BRCA2, and/or ATM (Cohort A), with a 66% reduction in risk for disease progression or death. Prespecified subgroup analyses for baseline demographics, disease and clinical characteristics showed a consistency of treatment effect in favor of olaparib compared with the control arm. Among patients with an alteration in BRCA1, BRCA2, and/or ATM, interim analysis of OS (secondary endpoint) showed favorable, though not statistically significant, benefit for the olaparib arm; this was observed despite >80% crossover to olaparib among the control arm patients whose disease had progressed. The delay in pain progression in the olaparib arm supplements the radiographic endpoints, demonstrating a direct patient benefit for olaparib compared with the control arm among patients with an alteration in BRCA1, BRCA2, and/or ATM.

Median total duration of assigned treatment for patients in the overall population (Cohorts A+B) was 7.4 months (range, 0 to 22.7) for olaparib and 3.9 months (0.6 to 19.5) for the control arm. The incidence of grade ≥3 AEs irrespective of attribution, dose modification, and treatment discontinuation owing to AEs was higher with olaparib than with the control treatment (Table 4). The most common AEs (≥10% of patients in either arm) of any grade were anemia, nausea and fatigue/asthenia with olaparib, and fatigue/asthenia with the control treatment. There were 11 (4.3%) pulmonary embolism events reported in the olaparib arm compared with one (0.8%) in the control arm; none were fatal. There were no reports of myelodysplastic syndromes or acute myeloid leukemia. Three patients reported new primary malignancies (olaparib, n=1; control, n=2). One death in each arm was reported to be related to study treatment.

TABLE 4

Summary of Adverse Events in the Overall Population (Cohorts A + B)

| n (%) | Olaparib (N = 256) | | Control arm (N = 130) | |
|---|---|---|---|---|
|  | All grades | Grade ≥3 | All grades | Grade ≥3 |
| Adverse event | | | | |
| Any | 244 (95.3) | 130 (50.8) | 114 (87.7) | 49 (37.7) |
| Anemia[†] | 118 (46.5) | 55 (21.5) | 20 (15.4) | 7 (5.4) |
| Nausea | 106 (41.4) | 3 (1.2) | 25 (19.2) | 0 |
| Fatigue & asthenia | 105 (41.0) | 7 (2.7) | 42 (32.3) | 7 (5.4) |
| Decreased appetite | 77 (30.1) | 3 (1.2) | 23 (17.7) | 1 (0.8) |
| Diarrhea | 54 (21.1) | 2 (0.8) | 9 (6.9) | 0 |
| Vomiting | 47 (18.4) | 6 (2.3) | 16 (12.3) | 1 (0.8) |
| Constipation | 45 (17.6) | 0 | 19 (14.6) | 0 |
| Back pain | 35 (13.7) | 2 (0.8) | 15 (11.5) | 2 (1.5) |
| Peripheral edema | 32 (12.5) | 0 | 10 (7.7) | 0 |
| Cough | 28 (10.9) | 0 | 3 (2.3) | 0 |
| Dyspnea | 26 (10.2) | 6 (2.3) | 4 (3.1) | 0 |
| Arthralgia | 24 (9.4) | 1 (0.4) | 14 (10.8) | 0 |
| Urinary tract infection | 18 (7.0) | 4 (1.6) | 15 (11.5) | 5 (3.8) |

TABLE 4-continued

Summary of Adverse Events in the Overall Population (Cohorts A + B)

| n (%) | Olaparib (N = 256) | | Control arm (N = 130) | |
|---|---|---|---|---|
| | All grades | Grade ≥3 | All grades | Grade ≥3 |
| Interruption of intervention due to adverse event | 115 (44.9) | N/A | 24 (18.5) | N/A |
| Dose reduction due to adverse event | 57 (22.3) | N/A | 5 (3.8) | N/A |
| Discontinuation of intervention due to adverse event | 46 (18.0) | N/A | 11 (8.5) | N/A |
| Fatal adverse event | 10 (3.9) | N/A | 5 (3.8) | N/A |

There was also a statistically significant and clinically meaningful improvement in rPFS for olaparib compared with the control treatment in the overall population (patients with an alteration in any of the 15 prespecified genes with a direct or indirect role in HRR), although this may have been in part due to the benefit seen in a subset of patients including the population with BRCA1 and/or BRCA2 alterations. This treatment benefit was supported by findings for overall survival and other clinical endpoints in this broader HRR population.

Patients received olaparib for nearly twice as long as the control arm, which may have contributed to the higher rate of certain adverse events (AEs) for example peripheral edema, back pain, and constipation in the olaparib arm. The safety profile of olaparib was similar to that described in other monotherapy studies. Pulmonary embolism is not a recognized complication of olaparib treatment and the significance of the occurrence of these events is difficult to interpret. Physician's choice of either enzalutamide or abiraterone was selected as the comparator as switching to one of these agents does occur in practice, despite the absence of randomized evidence to support this. The present study included both chemotherapy-naïve and chemotherapy-treated patients, with two-thirds having previously received taxane therapy. Efficacy in Cohort A and the overall population was seen regardless of whether olaparib monotherapy was administered prior to or post-chemotherapy.

In men with mCRPC selected for BRCA1, BRCA2, and/or ATM mutations and previously treated with NHA, olaparib led to a clinically meaningful and significant prolongation of rPFS when compared with physician's choice of enzalutamide or abiraterone. A benefit was also observed in the overall study population with an alteration in any of the 15 prespecified genes with a direct or indirect role in HRR. The most frequent AEs reported in the study were consistent with the known safety profile of olaparib.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A method for delaying pain progression in a subject receiving treatment for prostate cancer, the method comprising:
   administering to the subject a therapeutically effective amount of 4-[(3-{[4-(cyclopropane-carbonyl) piperazine-1-yl]carbonyl}-4-fluorophenyl) methyl]-2H-phthalazin-1-one (olaparib), or a hydrate, solvate, or prodrug thereof, wherein the therapeutically effective amount of olaparib is about 600 mg daily; then
   identifying the subject as having pain progression as evaluated by a pain questionnaire or an opioid use log and administering to the subject a therapeutically effective amount of an opiate;
   wherein the time to pain progression in the subject is delayed by at least 10 months as compared to the time to pain progression in a subject receiving the standard of care treatment; and
   wherein the administration of the opiate to the subject is delayed by at least 10 months as compared to administration of an opiate in a subject receiving the standard of care treatment.

2. The method of claim 1, wherein the cancer metastasized.

3. The method of claim 2, wherein the metastasis is to bone.

4. The method of claim 1, wherein the cancer is metastatic castration-resistant prostate cancer (mCRPC).

5. The method of claim 1, wherein the cancer cells comprise one or more homologous recombination repair (HRR) gene mutations.

6. The method of claim 1, wherein the cancer is metastatic castration-resistant prostate cancer (mCRPC) comprising one or more homologous recombination repair (HRR) gene mutations.

7. The method of claim 5, wherein the HRR gene mutation is selected from BRCA1, BRCA2, ATM, BRIP1, BARD1, CDK12, CHEK1, CHEK2, FANCL, PALB2, PPP2R2A, RAD51B, RAD51C, RAD51D, and RAD54L gene mutation.

8. The method of claim 1, wherein the cancer cells comprise a BRCA1, a BRCA2, and/or an ATM gene mutation.

9. The method of claim 1, wherein the cancer cells comprise a BRIP1, a BARD1, a CDK12, a CHEK1, a CHEK2, a FANCL, a PALB2, a PPP2R2A, a RAD51B, a RAD51C, a RAD51D, and/or a RAD54L gene mutation.

10. The method of claim 1, wherein the subject previously did not receive taxane-based chemotherapy.

11. The method of claim 1, wherein the subject previously received taxane-based chemotherapy.

12. The method of claim 1, wherein the subject previously received new hormonal agent chemotherapy.

13. The method of claim 12, wherein the new hormonal agent is enzalutamide or abiraterone.

14. The method of claim 1, wherein the cancer is metastatic castration-resistant prostate cancer (mCRPC) comprising one or more homologous recombination repair (HRR) gene mutations, and wherein the subject previously received enzalutamide or abiraterone.

15. The method of claim 1, wherein the therapeutically effective amount of olaparib is about 300 mg twice daily.

16. The method of claim 1, further comprising identifying the subject as having cancer cells comprising one or more HRR gene mutations.

17. The method of claim 1, wherein the standard of care is treatment with a new hormonal agent.

18. The method of claim 1, wherein the therapeutically effective amount of the opiate is less than the therapeutically effective amount of an opiate in a subject receiving the standard of care treatment.

* * * * *